(12) United States Patent
Wang et al.

(10) Patent No.: US 11,160,841 B2
(45) Date of Patent: Nov. 2, 2021

(54) METHOD OF TREATING A DISEASE ASSOCIATED WITH POTASSIUM ION CHANNEL

(71) Applicant: SHANXI MOMENTUM PHARMACEUTICAL CO., LTD., Shaanxi (CN)

(72) Inventors: Baoan Wang, Shanxi (CN); Peng Mao, Shanxi (CN)

(73) Assignee: SHANXI MOMENTUM PHARMACEUTICAL CO., LTD., Shanxi (CN)

( * ) Notice: Subject to any disclaimer, the term of this patent is extended or adjusted under 35 U.S.C. 154(b) by 0 days.

(21) Appl. No.: 15/573,583

(22) PCT Filed: May 12, 2016

(86) PCT No.: PCT/CN2016/081796
§ 371 (c)(1),
(2) Date: Nov. 13, 2017

(87) PCT Pub. No.: WO2016/180347
PCT Pub. Date: Nov. 17, 2016

(65) Prior Publication Data
US 2018/0133279 A1    May 17, 2018

(30) Foreign Application Priority Data

May 13, 2015 (CN) .......................... 201510243075.7

(51) Int. Cl.
| | |
|---|---|
| A61K 36/00 | (2006.01) |
| A61K 36/8968 | (2006.01) |
| A61P 9/06 | (2006.01) |
| A61K 36/076 | (2006.01) |
| A61K 36/185 | (2006.01) |
| A61K 36/258 | (2006.01) |
| A61K 36/282 | (2006.01) |
| A61K 36/484 | (2006.01) |
| A61K 36/489 | (2006.01) |
| A61K 36/736 | (2006.01) |
| A61K 36/752 | (2006.01) |
| A61K 36/8888 | (2006.01) |

(52) U.S. Cl.
CPC ........ *A61K 36/8968* (2013.01); *A61K 36/076* (2013.01); *A61K 36/185* (2013.01); *A61K 36/258* (2013.01); *A61K 36/282* (2013.01); *A61K 36/484* (2013.01); *A61K 36/489* (2013.01); *A61K 36/736* (2013.01); *A61K 36/752* (2013.01); *A61K 36/8888* (2013.01); *A61P 9/06* (2018.01); *A61K 2236/00* (2013.01)

(58) Field of Classification Search
CPC ....................................................... A61K 36/00
See application file for complete search history.

(56) References Cited

FOREIGN PATENT DOCUMENTS

| | | | |
|---|---|---|---|
| CN | 1634206 A | * | 7/2005 |
| CN | 104483408 A | | 4/2015 |
| CN | 104825782 | | 8/2015 |
| JP | H0789863 A | | 4/1995 |

OTHER PUBLICATIONS

Yuan, Siwen, "Observation on Sixty Cases of Rapid Arrhythmia Treated with Xinsuning 1-7 Capsules," Journal of Shandong University of Traditional Chinese Medicine, vol. 24, No. 4, 31 Jul. 31, 2000, pp. 290-293, with English abstract.

Lin, Lei et al., "26 Cases of Frequent Ventricular Procontraction Treated with Xinsuning 1-7, Capsules," People's Military Surgeon, vol. 54, No. 6, Jun. 1, 2011, pp. 512, with English abstract.

* cited by examiner

*Primary Examiner* — Qiuwen Mi
(74) *Attorney, Agent, or Firm* — Perry + Currier Inc.

(57) ABSTRACT

An application of a combination of traditional Chinese medicine in the preparation of a potassium ion channel modulating agent. The combination of traditional Chinese medicine is made up of traditional Chinese medicine raw materials according to the following weight proportion: Coptidis Rhizoma 250~450; Pinelliae Rhizoma 150~350; Poria 150~450; Aurantii Fructus Immaturus 62~265; Dichroae Radix 150~350; Nelumbinis Plumula 10~70; Sophorae Flavescentis Radix 150~350; Artemisiae Annuae Herba 150~350; Ginseng Radix Et Rhizoma 65~265; Ophiopogonis Radix 150~350; and Glycyrrhizae Radix Et Rhizoma 62~265.

6 Claims, 2 Drawing Sheets

METHOD OF TREATING A DISEASE ASSOCIATED WITH POTASSIUM ION CHANNEL

FIELD OF THE INVENTION

The invention relates to traditional Chinese medicine, specific relates to a combination of traditional Chinese medicine, particularly relates to an application of a combination of traditional Chinese medicine in the preparation of a potassium ion channel regulating agent.

BACKGROUND OF THE INVENTION

In researches of heart disease, the studies concerning on potassium channels is increasing. Potassium ion channel is a class of channels with the most subtypes and complex functions. Generally, it can be divided into five categories, including delayed rectifier potassium channels (Ikr), transient outward potassium channels, inward rectifier potassium channels (Kir), adenosine triphosphate sensitive potassium channels (KATP) and acetylcholine sensitive potassium channels (IKAch). These channels are closely related to the occurrence and development of arrhythmias.

The delayed rectifier potassium channels fall into three categories, including rapid activation of delayed rectifier potassium currents (Ikr), slowly activated delayed rectifier potassium currents (Iks), ultrarapid activated delayed rectifier potassium currents (Ikur). Ikr and Iks play an important role in regulating the termination of phase II platform and repolarization of phase III of action potential for cardiac myocytes. The abnormality, up/down regulation of Ikr and Iks channels may lead to arrhythmias. Therefore, Ikr and Iks channels are important targets for the occurrence of arrhythmias and antiarrhythmic drugs.

Kir, is mainly responsible for maintaining the resting potential of the cell membrane, and it is also the major current of repolarization phase III. It is consisted of two transmembrane subunits of four polymers, and it can be blocked by intracellular $Mg^{2+}$ and polyamines at positive potential. The transient outward potassium channels are the main membrane current involved in repolarization of cardiac action potential. The opened channels exhibit instantaneous net outward current, then close to form the action potential of phase I. It has a great influence on the duration and morphology of the action potential. For KATP, myocardial KATP is suppressed by intracellular physiological levels of ATP, and couple the cell metabolism and membrane potential. The inward rectifier mechanism involves the inhibition of channel open by the intracellular $Mg^{2+}$ and $Na^+$.

IKAch regulates heart rate, which exists in the pacemaker cells and atrial myocytes of sinoatrial node. The density of atrial IKAch is about six folds to that of the ventricles. IKAch activation could lead to hyperpolarization of membrane potential, and reduce the spontaneous activity of sinoatrial node and atrioventricular node pacemaker cells, delay the conduction of the atrioventricular node.

Arrhythmias is caused by abnormally excited or agitated outside the sinoatrial node, and the slowdown, blocking of excitive conduction, or conducting via abnormal channels, namely, the origin and/or conduction disturbances of cardiomotility could lead to the allorhythmia of heart beat. Arrhythmia is an important group of diseases in cardiovascular disease. It can attack on its own or with the onset of cardiovascular disease. It can attack suddenly and lead to sudden death or involvement of heart perseveratively to failure. Arrhythmia can be found in all kinds of organic heart disease, among them, coronary atherosclerotic heart disease (coronary heart disease), cardiomyopathy, myocarditis and rheumatic heart disease are more common, especially when heart failure or acute myocardial infarction occurs. The arrhythmia that occurs in patients with basic health or plant neurologic disorders is also not uncommon. The main causes of arrhythmia occurs are: Impulsive formation anomaly (The elevation of automaticity of ectopic rhythm point, post depolarization, and trigger activity), or impulse conduction abnormality (reentry), or both. Therefore, the treatment of arrhythmia should reduce the automaticity, post depolarization and eliminate the reentry.

At present, according to the main function channel and electrophysiological characteristics of drugs, a number of drugs with different chemical structures could be grouped into four categories: Class I: sodium channel blockers; Class II: adrenergic receptor antagonists; Class III: extended action potential duration drugs (potassium channel blockers); Class IV: calcium channel blockers. The main drugs for arrhythmia treatment in clinic are quinidine, lidocaine, mexiletine, amiodarone, verapamil and so on, which show certain curative effects but with obvious side effects and toxic side effects at the same time. In addition to chemicals, some traditional Chinese medicines have been invented. Patent with number of 200310122205.9 discloses Xinsuning capsule for the treatment of palpitation, which relates to the traditional Chinese medicine for treatment of ventricular premature beat and its preparation method. However, the application range is very limited, and the regulation on the potassium channel (prolong action potential duration) of the combination of traditional Chinese medicine has not been disclosed. The present patent is further studied on the basis of the original patent technology, and the effect of the combination on the regulation of potassium channels (prolongation of action potential duration) are confirmed, and it can be used for treatment of ventricular, atrial, or supraventricular arrhythmias, and for application in lowering blood sugar and blood pressure.

SUMMARY OF THE INVENTION

The technical problem of the present invention is to overcome the deficiencies mentioned above, to design and study the combination of traditional Chinese medicine to regulate the potassium channel (prolongation of action potential duration), and use it to treat ventricular, atrial, or supraventricular arrhythmias.

The invention provides an application of a combination of traditional Chinese medicine in the preparation of a potassium ion channel modulating agent.

The combination of traditional Chinese medicine stated in the present invention is composed of a traditional Chinese medicine as the active ingredients and pharmaceutic adjuvants.

The combination of traditional Chinese medicine stated in the present invention is made up of traditional Chinese medicine raw material according to the following weight proportion:

| | | | |
|---|---|---|---|
| Coptidis Rhizoma | 250~450 | Poria | 150~450 |
| Pinelliae Rhizoma | 150~350 | Aurantii Fructus Immaturus | 65~265 |
| Dichroae Radix | 150~350 | Ginseng Radix Et Rhizoma | 65~265 |
| Nelumbinis Plumula | 10~70 | Ophiopogonis Radix | 150~350 |
| Sophorae Flavescentis | 150~350 | Glycyrrhizae Radix Et | 65~265 |

-continued

| Radix | Rhizoma |
|---|---|
| Artemisiae Annuae Herba | 150~350 |

Preferably, the combination of traditional Chinese medicine stated in the present invention is made up of traditional Chinese medicine raw material according to the following weight proportion:

| | | | |
|---|---|---|---|
| Coptidis Rhizoma | 334 g | Sophorae Flavescentis Radix | 250 g |
| Pinelliae Rhizoma | 250 g | Artemisiae Annuae Herba | 250 g |
| Poria | 250 g | Ginseng Radix Et Rhizoma | 167 g |
| Aurantii Fructus Immaturus | 167 g | Ophiopogonis Radix | 250 g |
| Dichroae Radix | 250 g | Glycyrrhizae Radix Et Rhizoma | 167 g |
| Nelumbinis Plumula | 42 g | | |

The action mechanism of the combination of traditional Chinese medicine is to prolong the action potential duration, regulate potassium channels and inhibit various potassium currents. The combination of traditional Chinese medicine of the present invention could prolong the action potential interval of the myocardial cells, thereby prolong the refractory period of myocardial electrical activity. It has the function of inhibiting arrhythmia induced by excitatory reentry without toxic side effects.

The electrophysiological study has been carried out on myocardial cells for the combination of traditional Chinese medicine of the present invention. The results show that the combination of traditional Chinese medicine obviously prolongs the action potential interval of the myocardial cells, and has the function of regulating potassium channel. The results show that the drug obviously prolongs the action potential interval of the myocardial cells with the function of regulating potassium channel, and the efficacy is dose-dependent. The drug has no obvious effect on the action potential interval of the myocardial cells by regulating the potassium ion channel, when the drug concentration at 1 mg/ml by repeating four times, there is no significant difference compared with the control group. The drug shows obvious effect on the action potential interval of the myocardial cells by regulating the potassium ion channel, when the drug concentration at 2 mg/ml by repeating seven times, there is significant difference compared with the control group (P<0.05). The drug shows obvious effect on the action potential interval of the myocardial cells by regulating the potassium ion channel, when the drug concentration at 4 mg/ml by repeating seven times, there is significant difference compared with the control group (P<0.05).

Therefore, the combination of traditional Chinese medicine can be used for preparing potassium ion channel regulating agents.

Another aim of the present invention is to provide a preparation method of the combination of traditional Chinese medicine.

The method comprises the following steps:

(1) The foreign matters and non medicinal parts are picked out from Artemisiae Annuae Herba, Sophorae Flavescentis Radix, Glycyrrhizae Radix Et Rhizoma, Poria, Coptidis Rhizoma, Aurantii Fructus Immaturus, Dichroae Radix, Ginseng Radix Et Rhizoma, Pinelliae Rhizoma, Ophiopogonis Radix, and Nelumbinis Plumula, respectively, and then set aside until use;

(2) The foreign matters and non medicinal parts are picked out from Artemisiae Annuae Herba, Sophorae Flavescentis Radix, Glycyrrhizae Radix Et Rhizoma, Poria, Coptidis Rhizoma, Aurantii Fructus Immaturus, Dichroae Radix, Ginseng Radix Et Rhizoma, Pinelliae Rhizoma, respectively, and then rinsed with flowing water and cut into slices or segments; Ophiopogonis Radix is moistened with a flowing water then crashed as flate and set aside until use;

(3) The crude drugs of steps (1) and (2) are dried at 70~80° C. and set aside until use;

(4) Coptidis Rhizoma, Aurantii Fructus Immaturus, Dichroae Radix, Nelumbinis Plumula and Sophorae Flavescentis Radix are extracted by reflux with 60% ethanol for two times, add eight times amount of solvent for the first time and six times for the second time, 1.5 h for each time. Combined the extracts, filtrated, and the filtrate is concentrated in vacuum at 0.04 Kpa and recovered ethanol at 70° C., continued to condense to obtain thick paste with the relative density of 1.38 which measuring at 60° C., then dried into dry paste at 80° C. and set aside until use;

(5) Ginseng Radix Et Rhizoma, Pinelliae Rhizoma and Poria are extracted by reflux with 70% ethanol for two times, add eight times amount of solvent for the first time and six times for the second time, 2 h for each time. Combined extracts, filtrated, and the filtrate is additionally collected and set aside until use;

(6) The residue from step (4) is combined with Ophiopogonis Radix, Artemisiae Annuae Herba and Glycyrrhizae Radix Et Rhizoma, then decocted with water for two times, add ten times amount of water for the first time and eight times for the second time, 1 h for each time. Combined decoction, filtrated, the filtrate is concentrated to obtain liquid extract with the relative density ranging from 1.05 to 1.06 (80° C.) and then 95% ethanol is added to the alcohol content reaching 70%, stirred well and stand for 24 h. The supernatant is removed and filtered, collected the filtrate and set aside until use;

(7) Merged the filtrates of steps 4 and 5, the filtrate is concentrated in vacuum at 0.04 Kpa and recovered ethanol at 70° C., continued to condense to thick paste with the relative density of 1.38 (60° C.), then dried to dry extract at 80° C. and set aside until use;

(8) Combined dry extract of steps 4 and 7, and crushed into 100 mesh fine powder. A proper amount of dextrin is added, then mixed, packed into capsules or prepared preparation with medicinal excipients.

The combination of traditional Chinese medicine is made according to the conventional method, including tablets, capsules, granules, oral liquid, pills and other oral preparations. In the preparation process, excipients normally used in pharmaceutics are added, such as filling agent, adhesive, disintegrating agent, lubricant, flavoring agent, etc.

The present invention provides the application of combination of traditional Chinese medicine in preparing potassium ion channel regulating agent. The stated application is an application in preparing antiarrhythmic drugs.

The present invention provides the application of combination of traditional Chinese medicine in preparing potassium ion channel regulating agent. The stated application is an application in the preparation of drugs for the treatment of ventricular, atrial or ventricular arrhythmias.

The present invention provides the application of combination of traditional Chinese medicine in preparing potassium ion channel regulating agent. The stated application is an application in the preparation of drugs for prolonging the action potential duration, regulating potassium channel and inhibiting various potassium currents.

The combination of traditional Chinese medicine of the invention could prolong the action potential interval of the myocardial cells, thereby prolong the refractory period of myocardial electrical activity. It has the function of inhibiting arrhythmia induced by excitatory reentry without toxic side effects. The present invention provides a novel potassium ion channel modulator, and a new medicine for the treatment of ventricular, atrial or ventricular arrhythmias, and it has a good application prospect. The present invention is easy to be operated and suitable for large-scale production.

The abscissa indicates the duration of medication (Unit: min), the ordinate indicates the decay time of the action potential (Unit: msec). 1 indicates the duration of medication at 2 mg/ml is from 0.65 min to 10.16 min.

Figure 2:
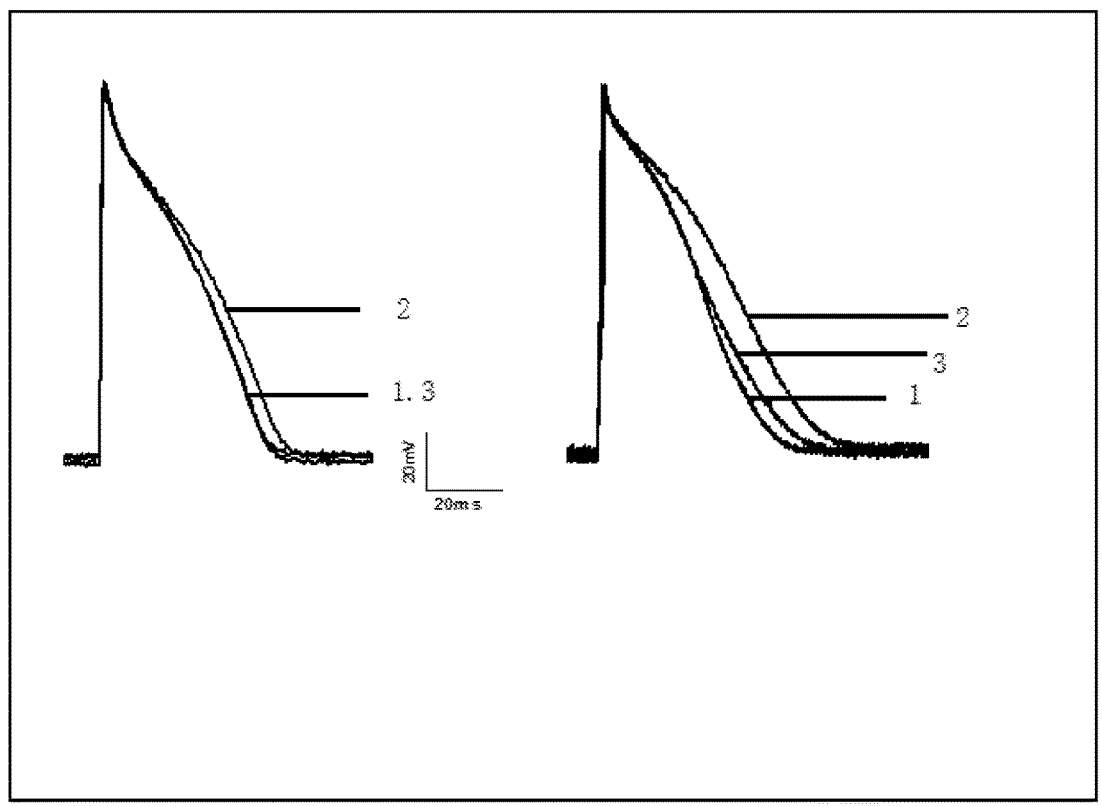

FIG. 2. The action potential diagram of the combination of traditional Chinese medicine at 2 mg/ml and 4 mg/ml.

The abscissa indicates the duration of medication (Unit: msec), the ordinate represents the action potential (Unit: mV). Line 1 indicates the relationship between the action potential and the time of the control group, and line 2 represents the relationship between the action potential and the time of the drug group (2 mg/ml), and line 3 indicates the relationship between the action potential and the time after washout of the cells.

Figure 3:
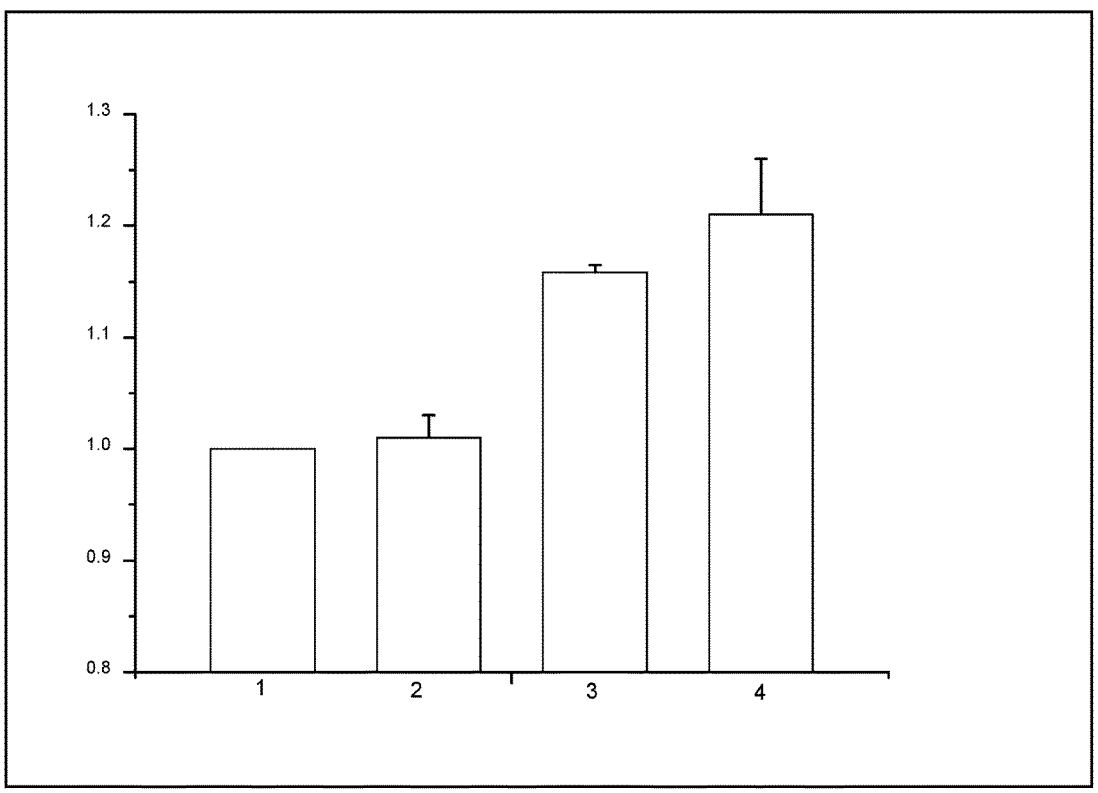

FIG. 3. The attenuation relationship of the action potential of the combination of traditional Chinese medicine at different concentrations (1 mg/ml, 2 mg/ml, and 4 mg/ml).

The abscissa indicates different concentration group, the ordinate indicates the action potential decrement. Column 1 is the attenuation of action potential of the control group, the attenuation of action potential is set to 1 in the control group. Column 2 is the attenuation of action potential of the drug group (1 mg/ml). Column 3 is the attenuation of action potential of the drug group (2 mg/ml). Column 4 is the attenuation of action potential of the drug group (4 mg/ml).

DETAIL DESCRIPTION OF PREFERRED EMBODIMENT

In order to facilitate the application of the combination of traditional Chinese medicine of the present invention to the electrophysiological study of cardiac myocytes, the combination of traditional Chinese medicine is prepared into freeze-dried powder or extract according to the proportion of prescriptions.

The traditional Chinese medicine raw materials used in the embodiment are commercially available.

Embodiment 1

[Prescription]

| Coptidis Rhizoma | 334 g | Sophorae Flavescentis Radix | 250 g |
|---|---|---|---|
| Pinelliae Rhizoma | 250 g | Artemisiae Annuae Herba | 250 g |
| Poria | 250 g | Ginseng Radix Et Rhizoma | 167 g |
| Aurantii Fructus Immaturus | 167 g | Ophiopogonis Radix | 250 g |
| Dichroae Radix | 250 g | Glycyrrhizae Radix Et Rhizoma | 167 g |
| Nelumbinis Plumula | 42 g | | |

1). The foreign matters and non medicinal parts are picked out from Artemisiae Annuae Herba, Sophorae Flavescentis Radix, Glycyrrhizae Radix Et Rhizoma, Poria, Coptidis Rhizoma, Aurantii Fructus Immaturus, Dichroae Radix, Ginseng Radix Et Rhizoma, Pinelliae Rhizoma, Ophiopogonis Radix, and Nelumbinis Plumula, respectively, and then set aside until use;

The foreign matters and non medicinal parts are picked out from Artemisiae Annuae Herba, Sophorae Flavescentis Radix, Glycyrrhizae Radix Et Rhizoma, Poria, Coptidis Rhizoma, Aurantii Fructus Immaturus, Dichroae Radix, Ginseng Radix Et Rhizoma, Pinelliae Rhizoma, respectively, and then rinsed (sprayed) or moistened (slightly moistened) with flowing water and cut into slices or segments; Ophiopogonis Radix is moistened with a flowing water then crashed as flate and set aside until use. Dried at 70~80° C.

2). Coptidis Rhizoma, Aurantii Fructus Immaturus, Dichroae Radix, Nelumbinis Plumula and Sophorae Flavescentis Radix are washed with 20 kg tap water for two times, and rinsed with 10 kg purified water for two times, then extracted by reflux with 60% ethanol for two times, add 8.4 L for the first time and 6.3 L for the second time, 1.5 h for each time. Combined extract, filtrated, and the filtrate is concentrated in vacuum at 0.04 Kpa and recovered ethanol at 70° C. Then 6.3 L injection water is added, heated at 50° C.~60° C., stirred to make it fully dissolved, filtrated while hot, stand for overnight, the supernatant is set aside until use;

3). Group B, Ginseng Radix Et Rhizoma, Pinelliae Rhizoma and Poria are washed with 13 kg tap water for two times, and rinsed with 6.5 kg purified water for two times, then extracted by reflux with 70% ethanol for two times, add 5.3 L for the first time and 4 L for the second time, 2 h for each time. Combined extract, filtrated, the filtrate and residue are set aside until use, respectively;

4). Group C, Ophiopogonis Radix, Artemisiae Annuae Herba and Glycyrrhizae Radix Et Rhizoma are washed with 13 kg tap water for two times, and rinsed with 6.5 kg purified water for two times, then combined with the residue in group B, decocted with injection water for two times, add 6.7 L for the first time and 5.3 L for the second time, 1 h for each time. Combined the filtrates for the second time and discarded the residue, the filtrate is concentrated to obtain liquid extract with the relative density ranging from 1.05 to 1.06 (80° C.) and then 95% ethanol is added to the alcohol content reaching 70%, stirred well and stand for 24 h. The supernatant is combined with the filtrate in group B, and recovered ethanol at 70° C. Then add 4 L injection water, heated at 50° C.~60° C., stirred to make it fully dissolved, filtrated while hot, stand for overnight, the supernatant is set aside until use;

5). Combined the supernatant of group A and C, then concentrated to obtain liquid extract with the relative density of 1.10 (60° C.) by rotating film evaporator and set aside until use;

6). Fixed the liquid extract with the relative density of 1.10 (60° C.) in pallet, freeze-dried for 20 h below −40° C. with the vacuum below 15 pa and the heating temperature from −20° C. to 80° C. Taken out and collected the freeze-dried solids, crushed, mixed, then 590 g lyophilized powder is obtained.

Embodiment 2

[Prescription]

| Coptidis Rhizoma | 334 g | Sophorae Flavescentis Radix | 250 g |
|---|---|---|---|
| Pinelliae Rhizoma | 250 g | Artemisiae Annuae Herba | 250 g |

| | | | |
|---|---|---|---|
| Poria | 250 g | Ginseng Radix Et Rhizoma | 167 g |
| Aurantii Fructus Immaturus | 167 g | Ophiopogonis Radix | 250 g |
| Dichroae Radix | 250 g | Glycyrrhizae Radix Et Rhizoma | 167 g |
| Nelumbinis Plumula | 42 g | | |

1). The foreign matters and non medicinal parts are picked out from Artemisiae Annuae Herba, Sophorae Flavescentis Radix, Glycyrrhizae Radix Et Rhizoma, Poria, Coptidis Rhizoma, Aurantii Fructus Immaturus, Dichroae Radix, Ginseng Radix Et Rhizoma, Pinelliae Rhizoma, Ophiopogonis Radix, and Nelumbinis Plumula, respectively, and then set aside until use;

The foreign matters and non medicinal parts are picked out from Artemisiae Annuae Herba, Sophorae Flavescentis Radix, Glycyrrhizae Radix Et Rhizoma, Poria, Coptidis Rhizoma, Aurantii Fructus Immaturus, Dichroae Radix, Ginseng Radix Et Rhizoma, Pinelliae Rhizoma, respectively, and then rinsed (sprayed) or moistened (slightly moistened) with flowing water and cut into slices or segments; Ophiopogonis Radix is moistened with a flowing water then crashed as flate and set aside until use. Dried at 70~80° C.

2). Coptidis Rhizoma, Aurantii Fructus Immaturus, Dichroae Radix, Nelumbinis Plumula and Sophorae Flavescentis Radix are washed with 20 kg tap water for two times, and rinsed with 10 kg purified water for two times, then extracted by reflux with 60% ethanol for two times, add 8.4 L for the first time and 6.3 L for the second time, 1.5 h for each time. Combined extract, filtrated, and the filtrate is concentrated in vacuum at 0.04 Kpa and recovered ethanol at 70° C. Then 6.3 L injection water is added, heated at 50° C.~60° C., stirred to make it fully dissolved, filtrated while hot, stand for overnight, the supernatant is set aside until use;

3). Group B, Ginseng Radix Et Rhizoma, Pinelliae Rhizoma and Poria are washed with 13 kg tap water for two times, and rinsed with 6.5 kg purified water for two times, and then extracted by reflux with 70% ethanol for two times, add 5.3 L for the first time and 4 L for the second time, 2 h for each time. Combined extract, filtrated, the filtrate and residue are set aside until use, respectively;

4). Group C, Ophiopogonis Radix, Artemisiae Annuae Herba and Glycyrrhizae Radix Et Rhizoma are washed with 13 kg tap water for two times, and rinsed with 6.5 kg purified water for two times, then combined with the residue in group B, decocted with injection water for two times, add 6.7 L for the first time and 5.3 L for the second time, 1 h for each time. Combined the filtrates for the second time and discarded the residue, the filtrate is concentrated to obtain liquid extract with the relative density ranging from 1.05 to 1.06 (80° C.) and then 95% ethanol is added to the alcohol content reaching 70%, stirred well and stand for 24 h. The supernatant is combined with the filtrate in group B, and recovered ethanol at 70° C. Then add 4 L injection water, heated at 50° C.~60° C., stirred to make it fully dissolved, filtrated while hot, stand for overnight, the supernatant is set aside until use;

5). Combined the supernatant of group A and C, then concentrated to obtain liquid extract with the relative density of 1.10 (60° C.) by rotating film evaporator and set aside until use;

6). Heated the liquid extract with the relative density of 1.10 (60° C.) in water bath into an extract without mobility, mixed, then it is obtained.

Embodiment 3

[Prescription]

| | | | |
|---|---|---|---|
| Coptidis Rhizoma | 334 g | Sophorae Flavescentis Radix | 250 g |
| Pinelliae Rhizoma | 250 g | Artemisiae Annuae Herba | 250 g |
| Poria | 250 g | Ginseng Radix Et Rhizoma | 167 g |
| Aurantii Fructus Immaturus | 167 g | Ophiopogonis Radix | 250 g |
| Dichroae Radix | 250 g | Glycyrrhizae Radix Et Rhizoma | 167 g |
| Nelumbinis Plumula | 42 g | | |

1). The foreign matters and non medicinal parts are picked out from Artemisiae Annuae Herba, Sophorae Flavescentis Radix, Glycyrrhizae Radix Et Rhizoma, Poria, Coptidis Rhizoma, Aurantii Fructus Immaturus, Dichroae Radix, Ginseng Radix Et Rhizoma, Pinelliae Rhizoma, Ophiopogonis Radix, and Nelumbinis Plumula, respectively, and then set aside until use;

The foreign matters and non medicinal parts are picked out from Artemisiae Annuae Herba, Sophorae Flavescentis Radix, Glycyrrhizae Radix Et Rhizoma, Poria, Coptidis Rhizoma, Aurantii Fructus Immaturus, Dichroae Radix, Ginseng Radix Et Rhizoma, Pinelliae Rhizoma, respectively, and then rinsed (sprayed) or moistened (slightly moistened) with flowing water and cut into slices or segments; Ophiopogonis Radix is moistened with a flowing water then crashed as flate and set aside until use. Dried at 70~80° C.

2). Coptidis Rhizoma, Aurantii Fructus Immaturus, Dichroae Radix, Nelumbinis Plumula and Sophorae Flavescentis Radix are washed with 20 kg tap water for two times, and rinsed with 10 kg purified water for two times, then extracted by reflux with 60% ethanol for two times, add 8.4 L for the first time and 6.3 L for the second time, 1.5 h for each time. Combined extract, filtrated, and the filtrate is concentrated in vacuum at 0.04 Kpa and recovered ethanol at 70° C. Then 6.3 L injection water is added, heated at 50° C.~60° C., stirred to make it fully dissolved, filtrated while hot, stand for overnight, the supernatant is set aside until use;

3). Group B, Ginseng Radix Et Rhizoma, Pinelliae Rhizoma and Poria are washed with 13 kg tap water for two times, and rinsed with 6.5 kg purified water for two times, then extracted by reflux with 70% ethanol for two times, add 5.3 L for the first time and 4 L for the second time, 2 h for each time. Combined extract, filtrated, the filtrate and residue are set aside until use, respectively;

4). Group C, Ophiopogonis Radix, Artemisiae Annuae Herba and Glycyrrhizae Radix Et Rhizoma are washed with 13 kg tap water for two times, and rinsed with 6.5 kg purified water for two times, then combined with the residue in group B, decocted with injection water for two times, add 6.7 L for the first time and 5.3 L for the second time, 1 h for each time. Combined the filtrates for the second time and discarded the residue, the filtrate is concentrated to obtain liquid extract with the relative density ranging from 1.05 to 1.06 (80° C.) and then 95% ethanol is added to the alcohol content reaching 70%, stirred well and stand for 24 h. The supernatant is combined with the filtrate in group B, and recovered ethanol at 70° C. Then add 4 L injection water, heated at 50° C.~60° C., stirred to make it fully dissolved, filtrated while hot, stand for overnight, the supernatant is set aside until use;

5). Combined the supernatant of group A and C, then concentrated to obtain liquid extract with the relative density of 1.10 (60° C.) by rotating film evaporator and set aside until use;

6). Heated the liquid extract with the relative density of 1.10 (60° C.) in water bath into an extract without mobility. Dried into dry extract at 80° C., crushed into 100 mesh powder, 200 g dextrin is added, mixed, then it is obtained by putting into capsules.

Embodiment 4

For the combination of traditional Chinese medicine in the present invention (lyophilized powder is obtained in embodiment 1), the electrophysiological test of myocardial cells is carried out.

1. Experimental Materials:
(1) Experimental Animals:
Male rats, weighting 250~500 g, was provided by the experimental animal center of University of Oxford.
(2) Drugs and Reagents
The test powder of the present invention is obtained in embodiment 1.
Precision weighing the test powder of the present invention and dissolved in the extracellular solution, the final concentration is 1 mg/ml, 2 mg/ml, 4 mg/ml, respectively. Reagents are purchased from Sigma Aldrich Co., Ltd (St. Louis, Mo., USA).
(1) Solution:
1) Extracellular Solution (mmol/L):
NaCl 112.0 g, KCl 10 g, $KH_2PO_4$ 1.2 g, HEPES 10 g, $MgSO_4$ 5 g, $NaHCO_3$ 15 g, Taurine 30 g, Glucose 20 g, $NaHCO_3$ 24.0 g (pH 7.4). Continuously pass into 5% $CO_2$ and 95% $O_2$.
2) Electrode solution (mmol/L): KCl 140 g, $MgCl_2$ 1 g, EGTA 5.0 g, Hepes 10.0 g, $Na_2ATP$ 2.0 g (pH 7.2).
2. Research Technique: Whole Cell Voltage Clamp Technique is Used to Record the Action Potential of Single Ventricular Myocyte, and to Make the Testing Drug Solution Act on Cells or Wash Out Cells by Continuously Infused.
1) Isolation of Single Ventricular Myocyte from Rats
Single ventricular myocyte is isolated from the heart of adult rats by enzyme digestion. The rats are stunned by the head crash, fixed on supine position after carotid artery bloodletting, and open the chest quickly and take out the heart. The heart is attached to the Waldorf perfusion system and the enzyme liquid is infused through the heart, and placed in calcium free solution at 36° C., continuously infused about 5 min. The constituents of calcium free solution are: NaCl 120 g, KCl 5.4 g, $MgSO_4$ 5 g, Pyruvic acid 5 g, Glucose 20 g, Taurine 20 g, HEPES 10 g (pH 6.96). The perfusate is added with 4 U/ml protease (Sigma type, XXIV) to replace calcium free perfusion solution. Infused for 2 min, the perfusate is switched again to the solution contained collagenase (Worthington 2, 0.3 mg/ml) and hyaluronidase (Sigma, 0.6 mg/ml). After 5 to 10 min, removed the heart from the cannula, discarded the atrium and cut the ventricles, put in a high potassium solution, the constituents are: (KOH 5 g, KCl 30 g, $KH_2PO_4$ 30 g, $MgSO_4$ 3 g, Glutamate 50 g, Taurine 20 g, EGTA 0.5 g, HEPES 10 g, Glucose 10 g (pH 7.4). The tissue should be filtered through four layers of gauze, the filtrate is centrifuged at 1500 rpm for 2 min Precipitated cells, discarded supernatant, potassium solution is added and centrifuged at 1500 rpm for 2 min, the cells are placed in a high potassium solution, kept at 4° C. until use.
2) Electrophysiological Techniques and Statistics
Put the separated cells into the cell bath, continuously infused (22~24° C.), the cell membrane potential is recorded by whole cell voltage clamp technique, and an 200B axonal patch clamp electrode amplifier with borosilicate glass electrode is used. The resistance is 1.5~3Ω, when the conductive liquid is added to the electrode. The current is recorded by 9th PCLAMPEX software (American Axon Corporation), PCLAMPFIt software (American Axon Corporation) for data analysis, and draw with Origin software (American, OriginLab Corporation). The drug is dissolved in the perfusate, administered after 3 min of infusion. The data are expressed as the mean SD, the effect of the drug is the difference between the control and administered groups. To compare the two groups, Student's t-test is employed.

Figure 1:
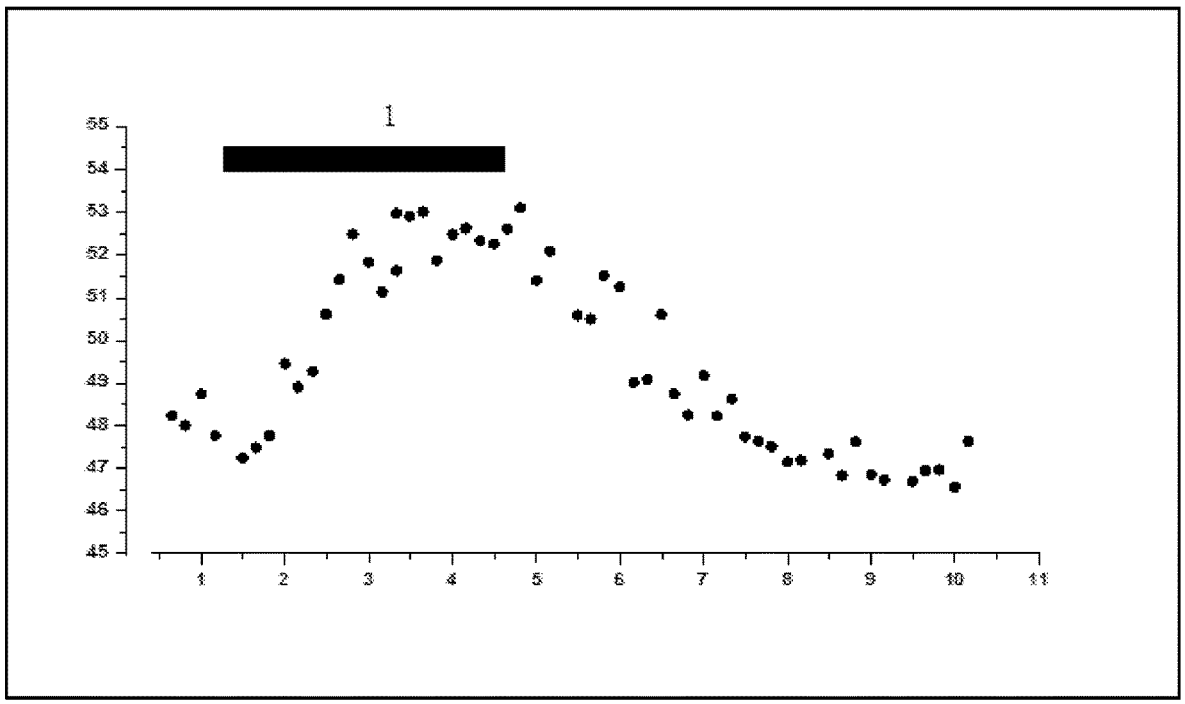
FIG. 1. The prolongation effects of the combination of traditional Chinese medicine at 2 mg/ml on the action potential.

3. Research Results:
(1) The results show that: the combination of traditional Chinese medicine obviously prolongs the action potential interval of the myocardial cells, and shows the function of regulating potassium channel: 45.4 ms±4.9 for control, 52.2 ms±4.5 (P<0.01, n=7) for the combination of traditional Chinese medicine (2 mg/ml). After administration of the drug, the action potential returns to the state before administration. As shown in FIG. 1, the results show that the drug obviously prolongs the action potential interval of the myocardial cells with the function of regulating potassium channel, and the efficacy is dose-dependent. The drug has no obvious effect on the action potential interval of the myocardial cells by regulating the potassium ion channel, when the drug concentration at 1 mg/ml in quadruplicate, there is no significant difference compared with the control group. The drug shows obvious effect on the action potential interval of the myocardial cells by regulating the potassium ion channel, when the drug concentration at 2 mg/ml in septuplicate, there is significant difference compared with the control group (P<0.05). The drug shows obvious effect on the action potential interval of the myocardial cells by regulating the potassium ion channel, when the drug concentration at 4 mg/ml in septuplicate, there is significant difference compared with the control group (P<0.05). The results are shown in FIGS. 2 and 3.

The invention claimed is:

1. A method of treating a disease associated with potassium ion channel in a subject, comprising:
preparing a traditional Chinese medicine composition, wherein the concentration of the traditional Chinese medicine composition is ≥2 mg/ml and the traditional Chinese medicine composition is made up of traditional Chinese medicine raw material according to the following weight proportion:

| Coptidis Rhizoma | 250~450 | Sophorae Flavescentis Radix | 150~350 |
| --- | --- | --- | --- |
| Pinelliae Rhizoma | 150~350 | Artemisiae Annuae Herba | 150~350 |
| Poria | 150~450 | Ginseng Radix Et Rhizoma | 65~265 |
| Aurantii Fructus Immaturus | 65~265 | Ophiopogonis Radix | 150~350 |
| Dichroae Radix | 150~350 | Glycyrrhizae Radix Et Rhizoma | 65~265, |
| Nelumbinis Plumula | 10~70 | | | wherein preparing the traditional Chinese medicine composition comprises:
(1) Picking The foreign matters and non medicinal parts out from Artemisiae Annuae Herba, Sophorae Flavescentis Radix, Glycyrrhizae Radix Et Rhizome, Poria, Coptidis Rhizoma, Aurantii Fructus Immaturus, Dichroae Radix, Ginseng Radix Et Rhizome, Pinelliae Rhizoma, Ophiopogonis Radix, and Nelumbinis Plumula, respectively, and then setting aside until use;
(2) Rinsing the residue from step (1) with flowing water and cutting into slices or segments; moistening Ophiopogonis Radix with a flowing water then crushing to be flat and setting aside until use;

(3) Drying The crude drugs of step (2) at 70~80° C. and setting aside until use;

(4) Extracting Coptidis Rhizoma, Aurantii Fructus Immaturus, Dichroae Radix, Nelumbinis Plumula and Sophorae Flavescentis Radix by reflux with 60% ethanol for two times, adding eight times amount of solvent for the first time and six times for the second time, 1.5 h for each time, combining the extracts, filtrating, and concentrating the filtrate in vacuum at 0.04 Kpa and recovering ethanol at 70° C., continuing to condense to obtain thick paste with the relative density of 1.38 when measured at 60° C., then drying into dry paste at 80° C. and setting aside until use;

(5) Extracting Ginseng Radix Et Rhizoma, Pinelliae Rhizoma and Poria by reflux with 70% ethanol for two times, adding eight times amount of solvent for the first time and six times for the second time, 2 h for each time, combining extracts, filtrating, and collecting the filtrate and setting aside until use;

(6) Combining The residue from step 5 with Ophiopogonis Radix, Artemisiae Annuae Herba and Glycyrrhizae Radix Et Rhizoma, then decocting with water for two times, adding ten times amount of water for the first time and eight times for the second time, 1 h for each time, combining decoction, filtrating, concentrating the filtrate to obtain liquid extract with the relative density ranging from 1.05 to 1.06 when measured at 80° C. and then adding 95% ethanol until the alcohol content reaches 70%, stirring well and standing for 24 h, removing and filtering the supernatant, collecting the filtrate and setting aside until use;

(7) Merging the filtrates of steps 5 and 6, concentrating the filtrate in vacuum at 0.04 Kpa and recovered ethanol at 70° C., continuing to condense to thick paste with the relative density of 1.38 when measured at 60° C., then drying to dry extract at 80° C. and setting aside until use; and (8) Combining the dry extract of steps 4 and 7 and crushing into 100 mesh fine powder, adding a proper amount of dextrin, then mixing, packing into capsules or prepared preparation with medicinal excipients; and administering an effective amount of the prepared traditional Chinese medicine composition to the subject.

2. The method of claim 1, wherein the disease is arrhythmia.

3. The method of claim 1, wherein the disease is ventricular, atrial or ventricular arrhythmia.

4. The method of claim 1, wherein the traditional Chinese medicine composition prolongs the action potential duration, regulates potassium channel and inhibits various potassium currents.

5. The method of claim 1, wherein the traditional Chinese medicine composition is a tablet, capsule, granule, oral liquid or pill.

6. A method of treating a disease associated with potassium ion channel in a subject comprising:
preparing a traditional Chinese medicine composition, wherein the concentration of the traditional Chinese medicine composition is ≥2 mg/ml and the traditional Chinese medicine composition is made up of traditional Chinese medicine raw material according to the following weight proportion:

| Coptidis Rhizoma | 334 g | Sophorae Flavescentis Radix | 250 g |
| Pinelliae Rhizoma | 250 g | Artemisiae Annuae Herba | 250 g |
| Poria | 250 g | Ginseng Radix Et Rhizoma | 167 g |
| Aurantii Fructus Immaturus | 167 g | Ophiopogonis Radix | 250 g |
| Dichroae Radix | 250 g | Glycyrrhizae Radix Et Rhizoma | 167 g, |
| Nelumbinis Plumula | 42 g | | | wherein preparing the traditional Chinese medicine composition comprises:

(1) Picking The foreign matters and non medicinal parts out from Artemisiae Annuae Herba, Sophorae Flavescentis Radix, Glycyrrhizae Radix Et Rhizoma, Poria, Coptidis Rhizoma, Aurantii Fructus Immaturus, Dichroae Radix, Ginseng Radix Et Rhizoma, Pinelliae Rhizoma, Ophiopogonis Radix, and Nelumbinis Plumula, respectively, and then setting aside until use;

(2) Rinsing the residue from step (1) with flowing water and cutting into slices or segments; moistening Ophiopogonis Radix with a flowing water then crushing to be flat and setting aside until use;

(3) Drying The crude drugs of step (2) at 70~80° C. and setting aside until use;

(4) Extracting Coptidis Rhizoma, Aurantii Fructus Immaturus, Dichroae Radix, Nelumbinis Plumula and Sophorae Flavescentis Radix by reflux with 60% ethanol for two times, adding eight times amount of solvent for the first time and six times for the second time, 1.5 h for each time, combining the extracts, filtrating, and concentrating the filtrate in vacuum at 0.04 Kpa and recovering ethanol at 70° C., continuing to condense to obtain thick paste with the relative density of 1.38 when measured at 60° C., then drying into dry paste at 80° C. and setting aside until use;

(5) Extracting Ginseng Radix Et Rhizoma, Pinelliae Rhizoma and Poria by reflux with 70% ethanol for two times, adding eight times amount of solvent for the first time and six times for the second time, 2 h for each time, combining extracts, filtrating, and collecting the filtrate and setting aside until use;

(6) Combining The residue from step 5 with Ophiopogonis Radix, Artemisiae Annuae Herba and Glycyrrhizae Radix Et Rhizoma, then decocting with water for two times, adding ten times amount of water for the first time and eight times for the second time, 1 h for each time, combining decoction, filtration, concentrating the filtrate to obtain liquid extract with the relative density ranging from 1.05 to 1.06 measured at 80° C. and then adding 95% ethanol until the alcohol content reaches 70%, stirring well and standing for 24 h, removing and filtering the supernatant, collecting the filtrate and setting aside until use;

(7) Merging the filtrates of steps 5 and 6, concentrating the filtrate in vacuum at 0.04 Kpa and recovering ethanol at 70° C., continuing to condense to thick paste with the relative density of 1.38 when measured at 60° C., then drying to dry extract at 80° C. and setting aside until use; and (8) combining the dry extract of steps 4 and 7 and crushing into 100 mesh fine powder, adding a proper amount of dextrin, then mixing, packing into capsules or prepared preparation with medicinal excipients; and administering an effective amount of the prepared traditional Chinese medicine composition to the subject.

* * * * *